United States Patent
Chen et al.

[11] Patent Number: 6,017,764
[45] Date of Patent: Jan. 25, 2000

[54] ERYTHROCYTE SEDIMENTATION RATE CONTROL

[75] Inventors: Roulhwai Chen, San Jose; Azra S. Zaidi, Cerritos, both of Calif.

[73] Assignees: Streck Laboratories, Inc., Omaha, Nebr.; Hematronix, Inc., Plano, Tex.

[21] Appl. No.: 09/294,506

[22] Filed: Apr. 20, 1999

Related U.S. Application Data

[63] Continuation of application No. 08/795,372, Feb. 4, 1997, Pat. No. 5,895,760.

[51] Int. Cl.[7] .................................................. G01N 31/00
[52] U.S. Cl. .................................... 436/10; 436/8; 436/16; 436/70; 252/408.1
[58] Field of Search ........................ 436/8, 10, 11, 436/16, 18, 68, 70; 435/2; 252/408.1; 422/73

[56] References Cited

U.S. PATENT DOCUMENTS

| | | | |
|---|---|---|---|
| 2,102,785 | 12/1937 | Brooks | 436/70 |
| 2,727,838 | 12/1955 | Dalter | 127/36 |
| 2,848,368 | 8/1958 | Witt | 73/61.65 |
| 2,929,764 | 3/1960 | Hultin et al. | 514/59 |
| 3,660,037 | 5/1972 | Sokol | 422/73 |
| 3,873,467 | 3/1975 | Hunt | 436/10 |
| 4,102,810 | 7/1978 | Armstrong | 436/16 |
| 4,264,470 | 4/1981 | Chastain, Jr. et al. | 436/10 |
| 4,299,726 | 11/1981 | Crews et al. | 436/10 |
| 4,324,686 | 4/1982 | Mundschenk | 436/10 |
| 4,358,394 | 11/1982 | Crews et al. | 436/10 |
| 4,489,162 | 12/1984 | Hawkins et al. | 436/10 |
| 4,572,899 | 2/1986 | Walker et al. | 436/18 |
| 4,704,364 | 11/1987 | Carver et al. | 436/10 |
| 4,777,139 | 10/1988 | Wong et al. | 436/18 |
| 5,328,822 | 7/1994 | McKinney et al. | 435/4 |
| 5,380,664 | 1/1995 | Carver et al. | 436/10 |
| 5,482,829 | 1/1996 | Kass et al. | 435/2 |
| 5,863,799 | 1/1999 | Hengstenberg | 436/10 |
| 5,888,822 | 3/1999 | Hengstenberg | 436/10 |

FOREIGN PATENT DOCUMENTS 01199158  8/1989  Japan.

OTHER PUBLICATIONS

Bull et al., The Zeta Sedimentation Ratio, Blood, 40(4):550 (Oct. 1972).
de Castro et al., Valoracion de un sistema alternativo totalmente automatizado para la determinacion de la velocidad de sedimentation globular, Sangre 34(1):4–9 (1989).
International Committee for Standardization in Heamatology (ICSH), Guidelines on selection of laboratory tests for monitoring the acute phase response, J. Clin. Pathol. 41:1203–1212 (1988).
International Committee for Standardization in Haematology (ICSH), Recommendation for Measurement of Erythrocyte Sedimentation Rate of Human Blood, Am. J. Clin. Pathol. 68:505–512 (1981).
International Committee for Standardization in Haematology (ICSH), Reference Method for the Erythrocyte Sedimentatin Rate (ESR) Test on Human Blood, Br. J. Haematol. 24:671 (1973).
Jou et al., Evaluacion de un sistema totalmente automatico para realizar la velocidad de sedimentacion globular, Sangre 33:474–478 (1988).
Product Brochure, DISPETTE®, Ulster Scientific, Inc., New Paltz, NY, date unknown.
Product Brochure, DISPETTE®2, Ulster Scientific, Inc., New Palz, NY, date unknown.
Todd–Sanford Clinical Diagnosis by Laboratory Method (15th edition), Erythrocyte Sedimentation Rate (ESR), edited by Davidsohn, I. and Henry, J., pp. 133–135, WB Saunders Company, London, Toronto (1974).

*Primary Examiner*—Maureen M. Wallenhorst

[57] ABSTRACT

A three-phase suspension suitable for use as an erythrocyte sedimentation rate (ESR) control having the following three components: (1) a synthetic plasma base, (2) an aggregating agent such as a high molecular weight polymer or combination of high molecular weight polymers, and (3) chemically fixed mammalian red blood cells. The control is designed to allow the user to monitor the accuracy and precision of analytical methods for determining the sedimentation rate of human erythrocytes in whole blood specimens. Chemical fixing of the red blood cells provides the ESR control with the capability of providing useful results in the presence of citrate and/or saline.

23 Claims, No Drawings

ERYTHROCYTE SEDIMENTATION RATE CONTROL

This application is a continuation of U.S. application Ser. No. 08/795,372, filed on Feb. 4, 1997, now U.S. Pat. No. 5,895,760 issued on Apr. 20, 1999. The priority of this prior application is expressly claimed and its disclosure is hereby incorporated by reference in its entirety.

FIELD OF THE INVENTION

This invention relates to the measurement of erythrocyte sedimentation rate (ESR), and more particularly to a blood control standard for the quality control of the measurement of ESR.

BACKGROUND OF THE INVENTION

The ESR test measures the sedimentation rate of aggregated erythrocytes in plasma. The rate of sedimentation is an indirect means of quantitating Rouleaux formation as well as red cell aggregation. Sedimentation occurs because the apparent surface/volume ratio of the red cells decreases and the denser Rouleaux overcome the buoyant forces of the plasma and sink. Erythrocyte sedimentation depends upon an interrelationship of a number of inherent biologic variables. Anything that increases the tendency to form Rouleaux or red cell aggregation will accelerate the sedimentation rate. In vivo, the plasma concentrations of proteins and globulins as well as the shape of the red blood cells are the most important factors contributing to the ESR.

In most normal persons, sedimentation takes place slowly, but in a variety of disease states the rate is rapid and in some cases proportional to the severity of the disease. The ESR test has been utilized as an indirect measure of these disease states. However, the test is very non-specific in that values for "normal" ESR may be influenced by local conditions as well as the age and sex of the patient. Nonetheless, the ESR test is an extremely common test which plays a significant role in contemporary medical practice.

Westergren developed the technique of performing an ESR determination as described in a paper published in 1924. See Alf Westergren, "Die senkungscreaktion", Ergegn. Inn. Med. Kinderheilk., 26:577 (1924). In the Westergren method, a blood sample is obtained by venepuncture and is thoroughly mixed with a suitable anticoagulant. Because the proteins and globulins in blood are unstable in vitro, at room temperature the test must be set up within 2 hours, or at $4_E$ C. within 6 hours. The blood-anticoagulant is thoroughly mixed by gentle repeated inversion and a clean dry standard Westergren-Katz tube is filled and adjusted to the '0' mark. The tube is then placed in a strictly vertical position under room temperature conditions ($18-25_E$ C.), not exposed to direct sunlight and free from vibrations and drafts. After a time period, usually 1 hour, the distance (x) from the bottom of the surface meniscus to the top of the column of sedimenting red cells (where the full density is apparent), is read in mm and recorded as the ESR value. The result is expressed as follows: 'ESR (Westergren 1 hr)=x mm'. Variations in the materials and methods are known, however, the basic technique is relatively unchanged since its introduction.

One variation of the Westergren method is a result of the substantial recent efforts directed to ways of decreasing the time involved in conducting the ESR test. Several ESR test apparatus manufacturers have developed methods of conducting ESR tests in less than one hour, e.g., 20 minutes or 30 minutes. These methods generally involve measuring the sedimentation distance after 20 or 30 minutes and converting that measurement to a one hour equivalent. Because the rate of sedimentation of a patient sample is generally exponential (i.e., nonlinear), this conversion involves something more than simply dividing the result by the fraction of one hour within which the measurement was made. Instead, these manufacturers have developed proprietary empirical conversion factors for converting a 20 or 30 minute measured value to a one hour standard value.

Due to the manner in which ESR is measured, in addition to the biologic variables certain identifiable environmental and technical factors may influence the ESR test in misleading ways. For example, the following factors may affect the measurement of ESR:

Environmental Factors:

1. Temperature. The room temperature during the test could lead to a misleadingly high ESR (higher temperatures) or low ESR (lower temperatures). Further, a variation of temperature during the test will also lead to misleading results.

2. Vibration. Vibration or movement of the testing apparatus during the test will result in misleading results.

Procedural Factors:

1. Positioning of tube. The correct or incorrect positioning of the tube at a perpendicular angle will affect test results.

2. Delay prior to test. A delay in performing the test beyond 2 hours of drawing the blood sample will create ambiguous results.

3. Insertion of tube in reservoir (for modified Westergren procedures). Failure to fully insert the tube to the bottom of the reservoir in certain modified Westergren procedures will affect the test results.

4. Unfamiliarity or failing to follow manufacturer's directions will affect test results.

Testing Materials Factors

1. Tube. Variations of the composition and/or length of the measurement tube will affect test results. For example, the use of glass vs. plastic tubes in either a Wintrobe or Westergren procedure will lead to variations in the observed sedimentation rate.

2. Anticoagulant. The anticoagulant used will affect test results.

3. Plasma. Changes in the plasma composition is a significant factor determining the measured ESR.

Before the commercial introduction in the mid-1990s of an ESR control product manufactured by Hycor Biomedical, Inc. of Garden Grove, Calif., there was no known commercial control by which the foregoing, and other, factors could be eliminated as sources affecting test results. Accordingly, a given ESR measurement could only be accepted as within a relatively large range of error. This decreased the significance of the ESR test.

Hycor's commercial ESR control product allowed users to monitor and verify the accuracy of their ESR test method and apparatus. However, it was found that chemical agents used in certain commercial ESR testing apparatus raised compatibility issues with the Hycor commercial product. In particular, in the presence of citrate, red blood cells in the Hycor ESR control were found to change their morphologies such that their sedimentation velocities were inhibited. A similar observation was made when the cells were in the presence of normal saline solution. These effects are significant because citrate and saline solution are commonly present in many commercially available ESR test apparatuses. It is therefore desirable to obtain an ESR control having the desirable properties described herein and which is compatible with citrate and/or saline.

Moreover, and as discussed above, many current commercially available ESR test apparatuses measure sedimentation rates over a time period of less than one hour, which is a departure from the standard Westergren technique. For example, the Ves-matic system (manufactured by Diesse Diagnostica Senese, Monteriggioni, Italy) and Sedimatic system (Analys Instrument AB, Stockholm, Sweden) measure ESR over periods of 20 minutes and 30 minutes, respectively, rather than one hour. Because of this, it is also desirable to obtain an ESR control that is capable of providing consistent and reproducible results for ESR test apparatuses that operate over measurement periods other than one hour.

SUMMARY OF THE INVENTION

The present invention is a reference control designed to monitor the accuracy and precision of analytical methods for determining the sedimentation rate of human erythrocytes in whole blood specimens.

In a first aspect, the ESR control comprises a three component colloidal/emulsion suspension: (1) a synthetic plasma base, (2) a polymer having a high molecular weight in the range of between 15,000–500,000, and (3) mammalian red blood cells. In the preferred embodiment, the polymer used is Dextran, a polysaccharide. Dextran is known for its use as a plasma expander used for cell separation, but is used for a different purpose in the ESR control of the present invention. Here, the addition of Dextran to the synthetic plasma base serves the function of behaving similar to an abnormal increase of large plasma proteins such as Fibrinogen and Alpha 2 macro-globulins in whole blood. It has been proposed that abnormal increases in plasma protein concentrations can cause an increase in aggregate formation resulting in an increased ESR. The Dextran and synthetic plasma base is a stable suspension that maintains the morphology of the red cells for long periods of time to allow for a controlled sedimentation of the cells. An ESR measurement using the ESR control should fall within a fairly narrow, predictable range. Measurements outside this range would therefore indicate flaws in the testing method.

In a second, separate aspect, the ESR control comprises a three component colloidal/emulsion suspension: (1) a synthetic plasma base, (2) a polymer or combination of polymers having high molecular weight(s), and (3) chemically fixed mammalian red blood cells. In the preferred embodiment, the polymers used are Dextran and polyethylene glycol. The use of fixed red blood cells provides the ESR control with the ability to operate in the presence of citrate or saline solution, which are commonly present in apparatuses used in the ESR test.

The ESR controls described above will advantageously provide sedimentation of red blood cells at a substantially constant (i.e., linear) rate. This is in contrast to the rate profile generally observed for a patient sample, which is generally exponential. The difference, however, is fairly inconsequential to the performance of these formulations as ESR controls. Because the sedimentation rate observed in the ESR control is substantially consistent and reproducible, the control is able to be used under any ESR test time period protocol and it will provide reproducible results.

For example, regardless of whether the ESR control is used in a manual system over a one hour protocol, or in an automated system measured over only 20 or 30 minutes, the ESR control will produce substantially consistent and reproducible ESR measurements for any given protocol, and is therefore suitable for use as a control for the given test method and apparatus.

DETAILED DESCRIPTION OF PREFERRED EMBODIMENTS

A number of subheadings are provided in the following discussion in order to provide organization and clarity.

1. Background and Theory

The ESR control of the present invention can be better understood if certain aspects of the phenomenon of sedimentation of erythrocytes in whole blood are described. Accordingly, a discussion of erythrocyte sedimentation and the theory of the ESR control are presented.

As previously discussed, the composition of the plasma is one of the two most important factors in determining erythrocyte sedimentation rate (the other being the shape of the red blood cells). The components in the plasma which create the Rouleaux effect and red cell aggregation are the plasma proteins and colloids, particularly the Fibrinogen, Alpha 1 and Alpha 2 globulins found in whole blood. It is known that all proteins affect the dielectric coefficient of plasma, but asymmetrical macromolecules are oriented by the field and hence exert a disproportionately large effect. Therefore, as fibrinogen and gamma globulin in plasma increase, they decrease the zeta potential of suspended red cells, permitting increased rouleaux formation and more rapid sedimentation rate. See Brian S. Bull and J. Douglas Brailsford, "The Zeta Sedimentation Ratio", *Blood* 1972:40:550. The ideal control would therefore incorporate these colloids and proteins. However, the chemistry of these components makes them unstable for any extended period of time, and would therefore limit the useful life of a control that included these components.

The use of high molecular weight polymers such as Dextran and polyethylene glycol in a synthetic plasma base serves to mimic the function of the Fibrinogen, Alpha 1 and Alpha 2 globulins found in whole blood by creating the Rouleaux effect. The two-phase high molecular weight polymer/synthetic plasma suspension therefore behaves similarly to natural plasma with the advantage of being a stable compound. Unlike the plasma proteins and colloids, Dextran and polyethylene glycol are stable in synthetic plasma.

The second important factor in accelerated erythrocyte sedimentation is the morphology of the cells. As fresh cells are allowed to sit in an EDTA or Sodium Citrate solution, they tend to crenate and manifest the phenomenon of anisocytosis and poikilocytosis along with exhibiting changes in the electrical charges on the surfaces of the red cells. Each of these changes tends to inhibit the sedimentation velocity. However, the high molecular weight polymer/synthetic plasma base suspension has been found to maintain the morphology of pre-treated, stabilized cells for long periods of time to allow for a controlled precipitation of the erythrocytes. The synthetic plasma base which bathes the mammalian red cells appears to cause no variation of size and shape of the cells, thereby allowing the cells to maintain a constant morphology.

In one aspect of the ESR control, the red blood cells of the ESR control are chemically fixed by pre-treatment in, for example, a glutaraldehyde solution. Chemical fixation of the cells in a glutaraldehyde solution causes substantial cross-linking of amino groups on the cell membrane surfaces both on individual cell surfaces and between cells. Accordingly, after fixing, cell membranes are less flexible and more stable. Accordingly, the morphologies of fixed cells do not change substantially in the presence of citrate and/or saline, unlike unfixed cells. Moreover, cross-linking of chemical groups on separate cells causes additional aggregation of cells.

2. Components

Turning now to the components and composition of the ESR control of the present invention, in a first aspect, the control comprises a three component colloidal/emulsion suspension: (1) a synthetic plasma base, (2) a polymer or combination of polymers having high molecular weights substantially in the range of between 15,000–500,000, and (3) pre-treated, stabilized mammalian red blood cells. In a second aspect, the mammalian red blood cells are fixed by treatment in, for example, glutaraldehyde. The three component colloidal/emulsion suspension is intended for use as a control for a given ESR test apparatus and method.

The ESR control is intended to exhibit the characteristics of a sample of human blood for the purpose of performing an ESR test. The components of the ESR control are therefore formulated to mimic these characteristics of human blood, such that there is provided a suspension that simulates an actual patient sample and that produces reproducible sedimentation rates within a predictable range of values. Commercially useful embodiments of the ESR control are further advantageously formulated to be stable for periods of prolonged storage.

a. Synthetic Plasma Base

The synthetic plasma base component of the ESR control is a carrying media that substitutes for plasma in natural blood and that maintains a homeostatic environment for the other components of the ESR control, particularly the red blood cells. For use in the ESR control, the synthetic plasma base comprises a carrying media that, in conjunction with the other components of the ESR control, produces predictable and reproducible red blood cell sedimentation rate values for a given ESR testing apparatus and method. In commercial ESR control products, it is preferable that the synthetic plasma base be formulated to stabilize the red blood cells and to maintain the morphology and specific gravity of the red blood cells, thereby conferring long-term stability on the ESR control.

To produce predictable and reproducible sedimentation rates in the ESR control, it has been found that Alsever's solution or a modified Alsever's solution-type synthetic plasma base is suitable for use as the synthetic plasma base component. It has been found that an ESR control having Alsever's solution as the synthetic plasma base component does not form a colloidal emulsion/suspension since the high molecular weight polymer component tends to dissolve in the Alsever's solution, however, this occurrence does not significantly effect the performance of the ESR control. An ESR control which relies substantially on Alsever's solution as the synthetic plasma base will be suitable if the requisite stability does not exceed a few days. Alsever's solution is a transport media well known in the art, comprising 2.05 gm dextrose, 0.80 gm sodium citrate, 0.42 gm sodium chloride, and 0.05 gm citric acid in 100 ml distilled water. Alsever's solution is well known as a media having preservative properties and that is useful for suspending living cells or tissues under investigation in vitro. As noted, the use of Alsever's solution as the synthetic plasma base component will provide an ESR control that produces predictable and reproducible ESR measurements. However, in an ESR control product with extended shelf life, it is advantageous to provide an altered formulation for the synthetic plasma base which includes components which are known to provide improved cell stability and prolonged shelf life.

For example, the addition of buffers to the synthetic plasma base has been found to assist in maintenance of a relatively constant pH. Bactericides and fungicides may be added to assist in retarding the adverse effects of contamination prior to or during storage. Protein stabilizers and cryoprotectants may be added to contribute to cell stability. Those skilled in the art will recognize that these and other materials may be added to the synthetic plasma base to provide additional beneficial results while not inhibiting the performance of the ESR control.

Accordingly, as a practical matter it is preferable to include materials in the synthetic plasma base that contribute to the long-term stability of the ESR control. To achieve this end, the synthetic plasma base is provided with materials that maintain the morphology and integrity of the red blood cells to allow the red blood cells to mimic the behavior of red blood cells in vivo, and to do so even after prolonged periods of storage. In relation to the interaction between the synthetic plasma base and the red blood cells, the properties of a synthetic plasma base which make it suitable for use in a commercially practical ESR control are the following: (1) the synthetic plasma base stabilizes the red blood cells in a manner that maintains the cell membranes in a dynamic state (for unfixed cells), (2) the synthetic plasma base maintains the morphology of the red blood cells, and (3) the synthetic plasma base maintains the specific gravity of the red blood cells.

A preferred form of the synthetic plasma base for use in the commercially practical ESR control is a synthetic plasma base that is provided with one or more of the materials described above, such as antibiotics, antifungals, protein stabilizers, cryoprotectants, and buffers. The synthetic plasma base is preferably formulated to exhibit characteristics similar to human plasma, such as specific gravity, pH, and potassium and sodium ion concentrations.

An example of a synthetic plasma base having the above-described properties which has been found to be suitable for use in the ESR control is the synthetic plasma base having the formulation listed below in Table 1. The synthetic plasma base having the formulation described in Table 1 has been found to confer long term stability to the red blood cells in the ESR control. Those skilled in the art will recognize that other and further variations of this formulation will provide the properties referred to above that make a solution suitable for use as the synthetic plasma base of the ESR control.

TABLE 1

Synthetic Plasma Base For Use in ESR Control

| Component | Amount Per Batch |
|---|---|
| Distilled Water | 40 L |
| Reagent Alcohol | 1,400 ml |
| Sodium Chloride | 40 gm |
| Sodium Fluoride | 30 gm |
| Sodium Citrate | 288 gm |
| Citric Acid | 20 gm |
| Sodium Nitrate | 200 gm |
| 3-N-morpholino propane sulfonic acid (MOPS) | 80 gm |
| Potassium ferrocyanide | 24 gm |
| Sodium hydroxide | 12 gm |
| Polyethylene glycol (M.W. Approx. 3500) | 400 gm |
| Polyethylene glycol (M.W. Approx. 7000) | 2,400 gm |
| Methyl paraben | 40 gm |
| Ethyl paraben | 20 gm |
| Bovine serum albumin (BSA) Fraction V | 80 gm |
| Tetracycline | 12 gm |
| Streptomycin | 20 gm |
| Penicillin | 20 gm |
| Neomycin | 12 gm |
| NaOH or HCl | q.s. to pH 7.0 " .02 |
| NaCl or Distilled Water | q.s. to conductivity 10,300–10,600 |

All of the chemicals listed above are available from Sigma Chemical, St. Louis, Mo. For best results, the components of the synthetic plasma base listed in the table are added in the order listed. The complete formulation is then filtered through a $0.2\mu$ cartridge filter.

b. High Molecular Weight Polymer (Aggregating Agent)

The high molecular weight polymer component of the ESR control is intended to contribute to sedimentation of the red blood cells in the suspension by causing increased Rouleaux formation. In this way, the high molecular weight polymer functions as an aggregating agent, similarly to an abnormal increase of the Fibrinogen, Alpha 1 and Alpha 2 globulins which perform the same function in whole blood as noted above. It has been found that a high density inert molecule that is physiologically compatible with red blood cells will tend to increase the aggregation of red blood cells in such a manner. Increased aggregation of red blood cells is believed to be caused by the polymer component of the ESR control due to the same physical and electrical mechanism by which the plasma proteins and colloids contribute to red cell aggregation in whole blood.

In a first aspect, Dextran having a molecular weight of substantially between 15,000 and 500,000 is utilized as the high molecular weight polymer, though those skilled in the art will appreciate that other high density inert molecules might alternatively be used. Dextran is a polysaccharide having a chain-like structure comprising a combination of certain polymers of glucose. It is produced from sucrose by Leuconostoc bacteria. Dextran is stable to heat and storage and is soluble in water, making very viscous solutions. Dextran is known for its use as a blood plasma substitute or expander, and particularly for its use in this regard for cell separations.

In a second aspect, polyethylene glycol (molecular weight of substantially between 1,500 and 20,000) is utilized in combination with Dextran (molecular weight of substantially between 15,000 and 500,000) as the aggregating agent component of the ESR control. As discussed more fully below, it has been found that a combination of polyethylene glycol and dextran as the aggregating agent component of the ESR control provides substantially consistent and reproducible ESR measurements when chemically fixed red blood cells are used in the ESR control.

Dextran and polyethylene glycol have been found to be preferred materials for use in the ESR control because each causes Rouleaux formation while maintaining cell membranes and cell morphologies intact. However, it is proposed that the following additional polymers may be found to provide adequate results in the ESR control:

1. Ficoll (MW 70,000–400,000): A synthetic polymer made by copolymerization of sucrose and epichlorhydrin that is widely used as a density gradient centrifugation medium. It is also used as an immunologically inert carrier for low-molecular-weight haptens in immunological studies.

2. Cellulose: A high-molecular-weight polysaccharide comprising long unbranched chains of (1,4)-linked β-D-glucose residues. Cellulose is found in cell walls of higher plants and some fungi as microfibrils, in which the cellulose chains form crystalline micelles separated by regions of randomized amorphous cellulose.

3. Cyclodextrin: Any of a number of oligosaccharides based on glucopyrinose units that are linked to form a ring structure. The molecule consists of an apolar, electron-rich, hydrophobic interior with exterior sites available for hydrophilic interactions at the entrances to the internal cavity.

4. Agar: A complex polysaccharide produced by red algae. It contains the polysaccharides agarose and agaropectin. Agar is used in food manufacture and as a matrix for the culture of microorganisms.

5. Agarose: A polysaccharide gum obtained from seaweed composed of alternating (1,3)-linked D-galactose and (1,4)-linked 3,6-anhydro-D-galactose residues, as well as small amounts of D-xylose. Some of the D-galactose units are methylated at C-6. Agarose is used as a gel medium in chromatography or electrophoresis.

6. Starch: A high-molecular-weight polysaccharide consisting largely of D-glucose units linked through an α-(1, 4)-link, forming a spiral chain with only one terminal reducing moiety per chain. It consists of two fractions: amylose (25 percent) and amylopectin (75 percent). It is the major storage carbohydrate in higher plants, where it accumulates in the form of grains.

7. Polyvinylpyrolidone (PVP) (MW 10,000–360,000).

8. Percoll: A colloidal PVP coated with silica, used for cell separation and for tissue cultures.

9. Dimethylpolysiloxane (MW 770–116,500).

Those skilled in the art will recognize that other and further polymers in addition to the polymers described above would be suitable for use in the ESR control. The function of the high molecular weight polymer component of the ESR control is to increase red cell aggregation and to thereby contribute to red cell sedimentation. Accordingly, it is believed that any high density inert molecule that is physiologically compatible with red cells would be suitable for use in the ESR control. Those specific examples provided herein are intended to illustrate the types of molecules suitable for use, rather than to limit them.

C. Mammalian Red Blood Cells

An additional component of the ESR control is mammalian red blood cells. In a first aspect, a wide range of sizes of red blood cells are suitable for use in the ESR control, and typically the cell sizes will range over a standard Gaussian distribution curve having a mean cell volume (MCV) of about 85 cubic microns. This range of cell sizes is not critical, but is utilized in the preferred embodiment because the range approximates that of normal cells present in a drawn sample of human blood. In the preferred embodiment, the mammalian red blood cells are pre-treated by performing approximately three washings of the cells in the synthetic plasma base over an approximately 21 day period. Pre-treatment of the red blood cells stabilizes the cells and causes the cells to maintain their morphology such that the ESR control is stable over an extended period of time.

In a second aspect, the mammalian red blood cells utilized in the ESR control are fixed through pre-treatment in a fixing solution. In a preferred embodiment, the cells are pre-treated by three washings in normal saline solution (0.9% NaCl). The cells are then fixed according to the following procedure:

1. Mammalian red blood cells are washed by mixing with normal saline (0.9% NaCl) at a ratio of about 300 ml of blood and 700 ml normal saline. The mixture is subsequently centrifuged at 3,000 rpm for a period of thirty minutes to obtain a packed sample.

2. After aspirating the supernatant, the packed cells are mixed with an equal volume of 0.25% glutaraldehyde solution to achieve a final glutaraldehyde concentration of 0.125%. The mixture is incubated at ambient temperature for approximately one hour. The 0.25% glutaraldehyde solution used above is prepared by using a 25% solution diluted with normal saline (0.09% NaCl) at a ratio of one part of glutaraldehyde and 9 parts normal saline.

3. After one hour incubation, the glutaraldehyde fixed cell mixture is centrifuged at 3,000 rpm for thirty minutes before the supernatant is aspirated.

4. The packed "fixed" cells are further washed by following the procedure in the above step 1. The washing of the fixed cells is carried out two times, after which the supernatant is removed. The packed fixed cells are then ready for use in the ESR control.

The above example includes using a 0.125% glutaraldehyde solution to fix the cells. Those skilled in the art will recognize that other cross-linking agents are available that would serve the same function as glutaraldehyde. For example, essentially all chemicals that fall into the categories of imidoesters, homobifunctional N-hydroxysuccinimide (NHS) esters and heterobifunctional NHS esters will crosslink red blood cells. Moreover, glutaraldehyde concentrations other than 0.125% are possible. It has been found that a glutaraldehyde solution having any concentration between about 0.125% to 1% is suitable for use as a fixing solution for red blood cells used in the ESR control. It is proposed that both higher and lower concentrations would be equally suitable.

Due to cross-linking of chemical groups on the surfaces of cell membranes, red blood cells fixed as described above are resistant to changes in morphology due to contact with citrate and/or saline solution. Fixed cells are therefore advantageously able to be used with ESR apparatus that include citrate and/or saline solutions.

3. Preferred Compositions

A wide range of reproducible sedimentation rates is obtainable through modification of the percentages of the components included in the ESR control. In particular, modification of the percentages of the aggregating agent(s) used in the ESR control will affect the measured sedimentation rates. Modifications may also be made to the percentage of fixed cells utilized.

The following table illustrates four preferred embodiments of the ESR control in accordance with the present invention. The embodiments described below that utilize fixed cells are suitable for use with ESR test equipment that includes citrate and/or saline:

|  | EXAMPLE I | EXAMPLE II | EXAMPLE III | EXAMPLE IV |
|---|---|---|---|---|
| Synthetic Plasma Base | (Table 1) | (Table 1) | (Table 1) | (Table 1) |
| Dextran | 3% | 3% | 8% | 8% |
| Polyethylene Glycol | — | — | 1% | 1% |
| Mammalian Red Blood Cells | Unfixed 20 H'crit | Unfixed 15 H'crit | Fixed 20% | Fixed 30% |

In the above table, the amount of red blood cells present in the formulation is expressed in terms of Hematocrit ("H'crit") for Examples I and II, and percentage for Examples III and IV. Hematocrit may be measured either with a cell counter or microhematocrit centrifuge. The percentage value of red blood cells refers to a volume percentage of packed cells, obtained from the fixing procedure described above, relative to the synthetic plasma base.

The ESR controls having the compositions shown in Examples I and II above, which do not utilize fixed cells, are suitable for use in ESR test apparatuses that do not include citrate or saline. The ESR control shown in Example I will provide substantially consistent ESR measurements in a "High Normal" range, while the ESR control shown in Example II will provide measurements in an "Abnormal" range. Tables 2 and 3 below list the results (in mm) of precision studies performed using the two assay levels for these two Examples. Further, the tables provide results of ESR tests using the two levels of control with several manufacturers' testing apparatuses, two different testing methods (Westergren and Wintrobe), and two different tube materials (glass and plastic).

The ESR controls having the compositions shown in Examples III and IV above, which utilize fixed cells, are suitable for use in ESR test apparatuses that include citrate or saline. The ESR control shown in Example III will provide substantially reproducible ESR measurements in an "Abnormal" high range, while the ESR control shown in Example IV will provide measurements in a "Normal" range. Tables 4 and 5 below list the results (in mm) of precision studies performed using the two assay levels for these two Examples. Further, the tables provide results of ESR tests using the two levels of control with two different manufacturers' testing apparatuses: SediplastJ by LP Italiana SP, and Ves-MaticJ by Diesse. Each of these testing apparatuses is commercially available, and each is prepackaged with citrate as an anticoagulant.

TABLE 2

ESR Readings of "High Normal" Assay Level - Example I (Tests run at temperatures ranging $19_E$ C–$21_E$ C)

| MFR: | LP Italiana | Baxter | Baxter | Ulster | Baxter |
|---|---|---|---|---|---|
| METHOD: | Westerg. | Westerg. | Westerg. | Wintrobe | Wintrobe |
| MTL: | Plastic | Plastic | Glass | Plastic | Glass |
|  | 10 | 7 | 15 | 11 | 4 |
|  | 9 | 8 | 14 | 10 | 5 |
|  | 12 | 8 | 12 | 7 | 5 |
|  | 6 | 3 | 12 | 6 | 5 |
|  | 11 | 3 | 14 | 10 | 6 |
|  | 10 | 6 | 13 | 3 | 2 |
|  | 3 | 4 | 12 | 6 | 3 |
|  | 5 | 4 | 13 | 2 | 3 |
|  | 5 | 9 | 14 | 7 | 4 |
|  | 9 | 7 | 12 | 3 | 4 |
|  | 9 | 6 | 13 | 4 | 4 |
|  | 8 | 4 | 13 | 3 | 4 |
|  | 10 | 5 | 10 | 5 | 4 |
|  | 7 | 3 | 13 | 4 | 3 |
|  | 11 | 8 | 12 | 3 | 4 |
|  | 6 | 3 | 16 | 3 | 2 |
|  | 8 | 4 | 12 | 6 | 3 |
|  | 8 | 5 | 16 | 3 | 3 |
|  | 9 | 3 | 14 | 6 | 3 |
|  | 13 | 6 | 15 | 8 | 2 |
|  | 3 | 8 | 15 | 8 | 4 |
|  | 10 | 8 | 10 | 6 | 4 |
|  | 5 | 5 | 13 | 6 | 3 |
|  | 3 | 5 | 11 | 3 | 3 |
|  | 5 | 4 | 15 | 5 | 4 |
|  | 5 | 5 | 15 | 2 | 7 |
|  | 3 | 6 | 13 | 6 | 7 |
|  | 2 | 6 | 13 | 3 | 4 |
|  | 9 | 3 | 8 | 5 | 4 |
|  | 8 | 3 | 12 | 7 | 6 |
|  | 12 | 6 | 12 | 3 | 3 |
|  | 7 | 2 | 7 | 2 | 3 |
|  | 4 | 7 | 12 |  | 4 |
|  | 9 | 6 | 13 |  | 5 |
|  | 6 | 7 | 11 |  | 6 |
|  | 5 | 5 | 15 |  | 5 |
|  | 5 | 5 | 12 |  | 4 |
|  | 9 | 4 | 14 |  | 3 |
|  | 10 | 2 | 11 |  | 5 |
|  | 7 | 6 | 14 |  |  |
|  | 4 | 8 |  |  |  |
|  | 4 | 4 |  |  |  |
|  |  | 8 |  |  |  |
|  |  | 6 |  |  |  |
| NUMBER: | 42 | 44 | 40 | 32 | 39 |
| MEAN: | 7 | 5 | 13 | 5 | 4 |
| S.D.: | 3 | 2 | 2 | 2 | 1 |

TABLE 3

ESR Readings of "Abnormal" Assay Level - Example II
(Tests run at temperatures ranging $19_F$ C–$21_F$ C)

| MFR: | LP Italiana | Baxter | Baxter | Ulster | Baxter |
|---|---|---|---|---|---|
| METHOD: | Westerg. | Westerg. | Westerg. | Wintrobe | Wintrobe |
| MTL: | Plastic | Plastic | Glass | Plastic | Glass |
|  | 24 | 24 | 32 | 26 | 24 |
|  | 23 | 26 | 34 | 22 | 26 |
|  | 24 | 24 | 33 | 27 | 26 |
|  | 31 | 27 | 24 | 27 | 22 |
|  | 30 | 26 | 25 | 26 | 24 |
|  | 32 | 23 | 27 | 23 | 23 |
|  | 33 | 20 | 29 | 22 | 28 |
|  | 32 | 25 | 29 | 23 | 24 |
|  | 30 | 23 | 30 | 25 | 25 |
|  | 30 | 24 | 31 | 26 | 29 |
|  | 36 | 26 | 32 | 27 | 24 |
|  | 29 | 23 | 30 | 28 | 27 |
|  | 24 | 25 | 33 | 24 | 25 |
|  | 28 | 24 | 30 | 25 | 27 |
|  | 20 | 27 | 32 | 29 | 26 |
|  | 28 | 23 | 24 | 27 | 20 |
|  | 22 | 29 | 28 | 25 | 25 |
|  | 18 | 27 | 31 | 25 | 22 |
|  | 27 | 26 | 28 | 28 | 27 |
|  | 24 | 30 | 27 | 29 | 25 |
|  | 25 | 31 | 29 | 24 | 31 |
|  | 25 | 22 | 31 | 25 | 30 |
|  | 25 | 25 | 32 | 21 | 31 |
|  | 25 | 23 | 34 | 28 | 32 |
|  | 24 | 30 | 26 | 21 | 25 |
|  | 25 | 27 | 27 | 25 | 24 |
|  | 27 | 24 | 32 | 21 | 27 |
|  | 22 | 26 | 31 | 25 | 21 |
|  | 25 | 25 | 29 | 23 | 26 |
|  | 25 | 24 | 25 | 25 | 27 |
|  | 22 | 25 | 31 | 25 | 19 |
|  | 23 | 17 | 30 | 27 | 22 |
|  | 28 | 25 | 29 | 34 | 24 |
|  | 25 | 25 | 27 | 25 | 24 |
|  | 23 | 26 | 27 | 25 | 22 |
|  | 25 | 23 | 25 | 26 | 26 |
|  | 27 | 22 | 31 | 26 | 20 |
|  | 24 | 21 | 34 | 24 | 22 |
|  | 25 | 22 | 30 |  | 23 |
|  | 28 | 25 | 21 |  | 23 |
|  | 25 | 22 | 21 |  | 25 |
|  | 25 | 20 | 22 |  | 22 |
|  |  | 15 |  |  |  |
|  |  | 25 |  |  |  |
|  |  | 27 |  |  |  |
|  |  | 22 |  |  |  |
|  |  | 22 |  |  |  |
|  |  | 26 |  |  |  |
|  |  | 19 |  |  |  |
|  |  | 22 |  |  |  |
|  |  | 26 |  |  |  |
|  |  | 21 |  |  |  |
| NUMBER: | 42 | 52 | 42 | 38 | 42 |
| MEAN: | 26 | 24 | 29 | 25 | 25 |
| S.D.: | 4 | 3 | 3 | 3 | 3 |

TABLE 4

ESR Readings of "Abnormal" Assay Level - Example III
(ESR Control having 8% Dextran/1% PEG/20% Fixed Cells)

| TRIAL # | Sediplast | Sediplast | Ves-Matic | Ves-Matic |
|---|---|---|---|---|
| 1 | 22 | 25 | 61 | 56 |
| 2 | 28 | 20 | 59 | 58 |
| 3 | 26 | 20 | 59 | 59 |
| 4 | 20 | 25 | 58 | 60 |
| 5 | 30 | 20 | 60 | 58 |
| 6 | 21 | 25 | 61 | 61 |
| 7 | 26 | 20 | 58 | 59 |
| 8 | 22 | 24 | 53 | 59 |
| 9 | 22 | 24 | 64 | — |
| 10 | 28 | 20 | — | 58 |
| 11 | 26 | 20 | 57 | 54 |
| 12 | 20 | 25 | 57 | 56 |
| 13 | 24 | 22 | 60 | 53 |
| 14 | 22 | 24 | 57 | 56 |
| 15 | 20 | 25 | 50 | 57 |
| 16 | 26 | 26 | 55 | 56 |
| 17 | 28 | 26 | 57 | 56 |
| 18 | 25 | 24 | 61 | 61 |
| 19 | 26 | 22 | 59 | 59 |
| 20 | 26 | 25 | 60 | 58 |
| Mean | 24.40 | 23.10 | 58.21 | 57.58 |
| S.D. | 1.50 | 1.50 | 2.90 | 2.90 |
| CV % | 6.15 | 6.49 | 4.98 | 5.04 |

TABLE 5

ESR Readings of "Normal" Assay Level - Example IV
(ESR Control having 8% Dextran/1% PEG/30% Fixed Cells)

| TRIAL # | Sediplast | Sediplast | Ves-Matic | Ves-Matic |
|---|---|---|---|---|
| 1 | 2 | 3 | 1 | 6 |
| 2 | 3 | 4 | 5 | 5 |
| 3 | 2 | 2 | 7 | 4 |
| 4 | 2 | 3 | 5 | 5 |
| 5 | 4 | 2 | 1 | 6 |
| 6 | 5 | 2 | 1 | 7 |
| 7 | 2 | 6 | 5 | 4 |
| 8 | 1 | 3 | 6 | 7 |
| 9 | 2 | 4 | 6 | 6 |
| 10 | 2 | 2 | 5 | 7 |
| 11 | 3 | 3 | 6 | 7 |
| 12 | 2 | 3 | 6 | 6 |
| 13 | 2 | 2 | 3 | 5 |
| 14 | 2 | 3 | 6 | 9 |
| 15 | 2 | 3 | 6 | 7 |
| 16 | 2 | 5 | 5 | 7 |
| 17 | 5 | 6 | 6 | 5 |
| 18 | 2 | 3 | 6 | 7 |
| 19 | 2 | 3 | 7 | 8 |
| 20 | 5 | 4 | 4 | 7 |
| Mean | 2.60 | 3.30 | 4.85 | 6.25 |
| S.D. | 1.19 | 1.22 | 1.90 | 1.29 |

4. Method of Making

The following are examples of methods of making ESR controls in accordance with the present invention. As will be more fully discussed below, the molecular weights, concentrations, Hematocrit values and compositions are intended for exemplary purposes only, and are in no way intended to limit the scope of the present invention.

EXEMPLARY METHOD #1

One exemplary method comprises the following:

1. Prepare a solution of 3% Dextran (MW 184,000) in the synthetic plasma base. For example, add 30 grams of Dextran powder to 1000 ml of synthetic plasma base. The suspension should be mixed for at least 3 hours on a rotating mixer or with a magnetic mixer. Visually confirm that the powdered Dextran has dissolved.

2. Combine units of pre-treated red blood cells to approximate 1 liter. Centrifuge the units of pre-treated cells at 2000 rpm for 30 minutes at 5–10₍E₎ C. Extract as much of the supernatant necessary to yield a RBC count of 900,000 to 1,000,000 per cubic millimeter. (If no cell counter is available, utilize a microhematocrit centrifuge to verify a Hematocrit of 80% or more.)

3. Utilizing a graduated cylinder, pour 200 ml of the concentrated pre-treated red blood cells and q.s. to 1000 ml of the 3% Dextran/synthetic plasma base mixture. (Note: Each time the Dextran/synthetic plasma base mixture is used, it should be mixed by inversion, e.g. 10–15 times. This is a 2 phase suspension that will separate upon standing.)

4. Perform a Spun Hematocrit on the three component mixture and verify that it has a Spun Hematocrit of 20%" 1%. (Note: Each time the finalized product is tested for Hematocrit readings, be sure to mix by gentle inversion, e.g. 10–15 times. This is a 3 phase suspension that will separate upon standing.)

5. Pour the three phase suspension into a container which will accommodate greater than one liter. Make adjustments to the mixture by the addition of concentrated red blood cells or Dextran/synthetic plasma base mixture. This is a trial and error step that may require several additions to achieve the desired 20% Hematocrit value.

6. Keep the finished mixture refrigerated for 24 hours and verify that the Hematocrit is stabilized at 20%" 1%.

The ESR control produced by the foregoing process has the composition set forth in Example I above. As noted above, this assay level has been found to provide ESR readings in a "High Normal" range. The ESR control of Example II ("Abnormal") above may be obtained where the foregoing procedure is altered by changing the amount of concentrated pre-treated red blood cells added to 1000 ml of the 3% Dextran/synthetic plasma base mixture in step 3 from 200 ml to 150 ml, and then performing a Spun Hematocrit on the mixture in step 4 to obtain a Spun Hematocrit of 15%" 1%. Other levels of control are obviously possible by simply varying the amount of concentrated red blood cells used in step 3 to obtain different Spun Hematocrit values of the final product.

EXEMPLARY METHOD #2

A further exemplary method of making an ESR control in accordance with the present invention comprises the following:

1. Prepare a suspension of 8% Dextran (MW 184,000) and 1% polyethylene glycol (PEG) (MW 15,000–20,000) in the synthetic plasma base. For example, add 80 grams of Dextran powder and 10 grams of PEG to 1000 ml of synthetic plasma base. The suspension should be mixed for at least 3 hours on a rotating mixer or with a magnetic mixer. Visually confirm that the powdered Dextran and PEG have dissolved.

2. Prepare a 200 ml sample of fixed red blood cells by following the fixing procedure described above.

3. Utilizing a graduated cylinder, pour the 200 ml of the packed pre-treated, fixed red blood cells and q.s. to 1000 ml of the Dextran/PEG/synthetic plasma base mixture prepared in step 1. (Note: Each time the Dextran/PEG/synthetic plasma base mixture is used, it should be mixed by inversion, e.g. 10–15 times. This is a 2 phase suspension that will separate upon standing.)

The ESR control produced by the foregoing process has the composition set forth in Example III above. As noted above, this assay level has been found to provide ESR readings in an "Abnormal" range. The ESR control of Example IV ("Normal") above may be obtained where the foregoing procedure is altered by changing the amount of concentrated pre-treated red blood cells in step 3 from 200 ml to 300 ml added to q.s. 1000 ml of the Dextran/PEG/synthetic plasma base mixture. Other levels of control are obviously possible by simply varying the amount of concentrated fixed red blood cells used in step 3 to obtain different percentage values of red blood cells in the final product.

Using components having the molecular weights, concentrations, Hematocrit values and compositions in the methods and Examples described above will produce ESR controls in accordance with the present invention. However, significant departures from those values are possible while still remaining within the scope of the present invention. For example, in the following three examples utilizing unfixed cells, in which the Hematocrit value, Dextran concentration, and Dextran molecular weight are all varied, it is believed that the resulting suspensions will all produce an ESR control that provides an ESR reading of about 30 for a given test apparatus:

| HEMATOCRIT VALUE | DEXTRAN CONCENTRATION | DEXTRAN MW | ESTIMATED APPROX. ESR VALUE |
|---|---|---|---|
| 30 | 8% | 280,000 | 30 |
| 25 | 5% | 240,000 | 30 |
| 15 | 3% | 140,000 | 30 |

The purpose of the preceding examples is to demonstrate that it is the relative values of the Hematocrit, Dextran concentration and Dextran molecular weight utilized in the ESR control, rather than the values themselves, that are important to the effectiveness of the suspension as an ESR control. The purpose of the ESR control is to produce results in a predictable range of ESR values; accordingly, as long as the composition is such that consistent ESR values are obtained, the composition is useful as an ESR control. Those skilled in the art will recognize that other and further variations of the values listed above are possible.

While the above description contains many specificities, these should not be construed as limitations on the scope of the invention, but rather as an exemplification of a preferred embodiment thereof. Other variations are possible.

Accordingly, the scope of the present invention should be determined not by the embodiments illustrated above, but by the appended claims and their legal equivalents.

What is claimed is:

1. A method for preparing an erythrocyte sedimentation rate control comprising the steps of:
    a. preparing a suspension comprising an aggregating agent in a synthetic plasma base; and
    b. adding mammalian red blood cells to the suspension of step a. to obtain a suspension having a hematocrit value, wherein said mammalian red blood cells having been chemically fixed such that the morphologies of said cells are substantially resistant to change wherein sedimentation of the red blood cells within the suspension takes place at a substantially reproducible rate.

2. The method of claim 1, wherein said synthetic plasma base includes protein stabilizers.

3. The method of claim 1, wherein said synthetic plasma base includes cryoprotectants.

4. The method of claim 1, wherein said synthetic plasma base comprises antibiotics, antifungals, protein stabilizers, cryoprotectants and buffers.

5. The method of claim 1, wherein said synthetic plasma base comprises tetracycline, methyl paraben, albumin, glycol, and 3-N-morpholino propane sulfonic acid.

6. The method of claim 1, wherein said synthetic plasma base comprises about 0.3 g/l tetracycline, about 1.0 g/l methyl paraben, about 2.0 g/l albumin, about 70.0 g/l glycol, about 2.0 g/l 3-N-morpholino propane sulfonic acid, and q.s to 1 liter distilled water.

7. The method of claim 1, wherein said synthetic plasma base further comprises about 35 ml/l of reagent alcohol comprising one or more from the group consisting of methanol, ethanol and isopropanol.

8. The method of claim 1, wherein the suspension further comprises about 0.60 g/l potassium ferrocyanide.

9. The method of claim 1, wherein said aggregating agent is a chemically inert molecule that is physiologically compatible with red blood cells.

10. The method of claim 1, wherein said aggregating agent is a polysaccharide.

11. The method of claim 1, wherein said aggregating agent is one or more from the group consisting of Dextran, Ficoll, Cellulose, Cyclodextrin, Agar, Agarose, Starch, Polyvinylpyrolidone, Polyethylene Glycol, Percoll, and Dimethylpolysiloxane.

12. The method of claim 1, wherein said aggregating agent is dextran.

13. The method of claim 12, wherein said dextran has a molecular weight substantially in the range between 15,000 to 500,000.

14. The method of claim 12, wherein said dextran has a molecular weight substantially in the range between 125,000 to 275,000.

15. The method of claim 12, wherein said dextran has a concentration of between about 30–80 g/l in said synthetic plasma base.

16. The method of claim 1, wherein said mammalian red blood cells are pretreated by washing in said synthetic plasma base.

17. The method of claim 1, wherein the sizes of said mammalian red blood cells range over a standard Gaussian distribution curve with a mean cell volume of about 85 cubic microns.

18. The method of claim 1, wherein said mammalian red blood cells have a mean cell volume of between 80–90 microns.

19. The method of claim 1, wherein the hematocrit value is between about 15% to about 30%.

20. The method of claim 1, wherein the hematocrit value is about 15%.

21. The method of claim 1, wherein the hematocrit value is about 20%.

22. The method of claim 1, wherein said mammalian red blood cells are chemically fixed by having been treated with a crosslinking agent.

23. The method of claim 22, wherein said crosslinking agent is glutaraldehyde having a concentration by weight of between about 0.125% to about 1%.

* * * * *